(12) United States Patent
Marquais-Bienewald et al.

(10) Patent No.: US 7,731,985 B2
(45) Date of Patent: *Jun. 8, 2010

(54) 4-AMINOPYRIMIDINES AND THEIR USE FOR THE ANTIMICROBIAL TREATMENT OF SURFACES

(75) Inventors: Sophie Marquais-Bienewald, Hegenheim (FR); Werner Hölzl, Eschentzwiller (FR); Wolfgang Haap, Lörrach (DE); Andrea Preuss, Basel (CH); Andreas Mehlin, Rheinfelden (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 1572 days.

This patent is subject to a terminal disclaimer.

(21) Appl. No.: 10/507,800

(22) PCT Filed: Mar. 10, 2003

(86) PCT No.: PCT/EP03/02438

§ 371 (c)(1),
(2), (4) Date: Sep. 13, 2004

(87) PCT Pub. No.: WO03/077656

PCT Pub. Date: Sep. 25, 2003

(65) Prior Publication Data

US 2005/0143387 A1  Jun. 30, 2005

(30) Foreign Application Priority Data

Mar. 15, 2002 (EP) .................................. 02405201

(51) Int. Cl.
*A01N 25/00* (2006.01)
*A01N 43/58* (2006.01)
*C07D 471/00* (2006.01)

(52) U.S. Cl. .................. 424/405; 514/247; 544/279

(58) Field of Classification Search ...................... None
See application file for complete search history.

(56) References Cited

U.S. PATENT DOCUMENTS

| 4,435,402 | A | | 3/1984 | Tsuji et al. ................... 424/251 |
| 5,250,530 | A | | 10/1993 | Giencke et al. ............. 514/256 |
| 5,668,140 | A | * | 9/1997 | Schaper et al. .............. 514/269 |
| 6,207,668 | B1 | | 3/2001 | Braun et al. ................. 514/256 |
| 7,015,228 | B2 | * | 3/2006 | Haap et al. ................... 514/256 |

FOREIGN PATENT DOCUMENTS

| CA | 2 340 405 | * | 2/2000 |
| CA | 2340405 | | 2/2000 |
| EP | 0323757 | | 7/1989 |
| EP | 0407899 | | 1/1991 |
| EP | 0424125 | | 4/1991 |
| EP | 0519211 | | 12/1992 |
| EP | 1 254 903 A1 | * | 11/2002 |
| WO | 95/07278 | | 3/1995 |
| WO | WO 95/07278 | * | 3/1995 |
| WO | 99/61439 | | 12/1999 |

* cited by examiner

*Primary Examiner*—Humera N Sheikh
*Assistant Examiner*—Jeffrey T Palenik
(74) *Attorney, Agent, or Firm*—Joseph C. Suhadolnik

(57) ABSTRACT

A method is provided for the antimicrobial treatment of a surface which comprises the contacting a surface with substituted 4-aminopyrimidines.

12 Claims, No Drawings

4-AMINOPYRIMIDINES AND THEIR USE FOR THE ANTIMICROBIAL TREATMENT OF SURFACES

The present invention relates to substituted 4-aminopyrimidines, to the preparation of such compounds, and to the use of such compounds in the antimicrobial treatment of surfaces, as antimicrobial active substances against gram-positive and gram-negative bacteria, yeasts and fungi and also in the preservation of cosmetics, household products, textiles and plastics and for use in disinfectants.

The present invention relates to the use of 4-aminopyrimidines of formula

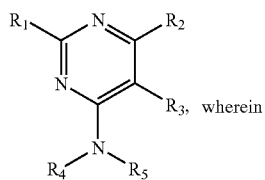

(1)

wherein $R_1$ and $R_2$ are each independently of the other hydrogen; $C_1$-$C_5$alkyl which is unsubstituted or substituted by one or more halogen atoms; biphenyl or $C_6$-$C_{10}$aryl which is unsubstituted or substituted by halogen, $C_1$-$C_5$alkyl, $C_1$-$C_5$alkoxy or by amino; a 5- to 7-membered heteroaryl radical; or cyclo-$C_3$-$C_7$alkyl;

$R_3$ is hydrogen; phenyl or $C_1$-$C_5$alkyl which is unsubstituted or substituted by one or more halogen atoms;

$R_4$ is hydrogen; $C_1$-$C_{10}$alkyl; phenyl; or a 5- to 7-membered heteroaryl radical;

$R_5$ is $C_1$-$C_{20}$alkyl which is unsubstituted or substituted by one or more halogen atoms or by a heterocyclic radical or interrupted by one or more —O— or

groups or by a bivalent heterocyclic radical; NR"R'"-$C_1$-$C_{10}$ alkyl which is unsubstituted or substituted by a heterocyclic radical or interrupted by one or more —O— or

groups or by a bivalent heterocyclic radical; cyclo-$C_5$-$C_8$alkyl; hydroxy-$C_1$-$C_{20}$alkyl; phenyl-$C_1$-$C_3$alkyl; a heterocyclic radical; or $R_4$ and $R_5$, together with the nitrogen atom linking them, form a radical of

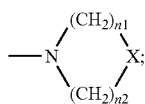

formula (1a)

R' is hydrogen; or $C_1$-$C_3$alkyl;

R" and R'" are each independently of the other hydrogen; $C_1$-$C_5$alkyl; or hydroxy-$C_1$-$C_5$alkyl;

X is

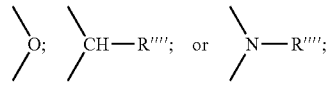

R"" is hydrogen; $C_1$-$C_4$alkyl; or heteroaryl-$C_1$-$C_4$alkyl; and $n_1$ and $n_2$ are each independently of the other from 1 to 8;

in the antimicrobial treatment of surfaces.

$C_1$-$C_{20}$Alkyl radicals are straight-chain or branched alkyl radicals, for example methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, pentadecyl, hexadecyl, heptadecyl, octadecyl or eicosyl.

$C_3$-$C_{10}$Cycloalkyl denotes, for example, cyclopropyl, cyclobutyl, cyclopentyl, cyclohexyl, cycloheptyl, cyclooctyl, cyclononyl or cyclodecyl. Those radicals may be substituted, for example by one or more identical or different $C_1$-$C_4$alkyl radicals, especially by methyl, and/or by hydroxy. When cycloalkyl radicals are substituted by one or more substituents, they are substituted preferably by one, two or four, especially by one or two, identical or different substituents.

$C_1$-$C_5$Alkoxy radicals are straight-chain or branched radicals such as, for example, methoxy, ethoxy, propoxy, butoxy or pentyloxy.

$C_6$-$C_{10}$Aryl and heteroaryl radicals may be unsubstituted or may carry one or more, for example one, two, three or four, identical or different substituents, which may be located in any positions. Examples of such substituents are, for example, $C_1$-$C_4$alkyl, halogen, hydroxy, $C_1$-$C_4$alkoxy, trifluoromethyl, cyano, hydroxycarbonyl, $C_1$-$C_4$alkoxycarbonyl, aminocarbonyl, amino, $C_1$-$C_4$alkylamino, di-$C_1$-$C_4$alkylamino and $C_1$-$C_4$alkylcarbonylamino.

Heteroaryl radicals are derived from heterocycles containing one, two, three or four identical or different ring hetero atoms, especially from heterocycles containing one, two or three, more especially one or two, identical or different hetero atoms. The heterocycles may be mono- or poly-cyclic, for example mono-, bi- or tri-cyclic. They are preferably mono- or bi-cyclic, especially monocyclic. The rings preferably contain 5, 6 or 7 ring members. Examples of monocyclic and bicyclic heterocyclic systems from which radicals occurring in the compounds of formula (1) can be derived are, for example, pyrrole, furan, thiophene, imidazole, pyrazole, 1,2,3-triazole, 1,2,4-triazole, pyridine, pyridazine, pyrimidine, pyrazine, pyran, thiopyran, 1,4-dioxane, 1,2-oxazine, 1,3-oxazine, 1,4-oxazine, indole, benzothiophene, benzofuran, pyrrolidine, piperidine, piperazine, morpholine and thiomorpholine.

Unsaturated heterocycles may contain, for example, one, two or three unsaturated double bonds in the ring system. 5-membered rings and 6-membered rings in monocyclic and polycyclic heterocycles may also be, especially, aromatic.

Halogen is fluorine, chlorine, bromine or iodine, preferably fluorine or chlorine.

In accordance with the invention, preference is given to the use of compounds of formula (1) wherein $R_5$ is R"R'"N—$C_1$-$C_{20}$alkyl which is uninterrupted or interrupted by one or more —O— or

groups or by a bivalent heterocyclic radical;
R' is hydrogen; or $C_1$-$C_5$alkyl;
R" and R'" are each independently of the other hydrogen; or methyl; and
$R_1$, $R_2$, $R_3$ and $R_4$ are as defined for formula (1).
Very special preference is given to the use of compounds of formula (1) wherein
$R_5$ is R"R'"N—$C_1$-$C_{20}$alkyl which is uninterrupted or interrupted by

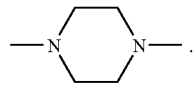

In accordance with the invention, there are furthermore used compounds of formula (1) wherein
$R_5$ is R"R'"N—$C_5$-$C_{20}$alkyl which is uninterrupted or interrupted by one or more —O— or

groups;
R' is hydrogen; or $C_1$-$C_5$alkyl; and
R" and R'" are each independently of the other hydrogen; or methyl.
Among those compounds, preference is given to those wherein
$R_5$ is R"R'"N—$C_1$-$C_5$alkyl; and
R" and R'" are each independently of the other hydrogen; or methyl.
Very special preference is also given to the use of compounds of formula (1) wherein
$R_4$ is hydrogen; or $C_1$-$C_5$alkyl;
$R_5$ is $C_5$-$C_{20}$alkyl which is unsubstituted or interrupted by —NH—; and
$R_1$, $R_2$ and $R_3$ are as defined for formula (1);
especially compounds of formula (1) wherein
$R_1$ is hydrogen; $C_1$-$C_5$alkyl; unsubstituted or $C_1$-$C_4$alkyl-substituted phenyl or phenyl-$C_1$-$C_4$alkyl; or pyridino;
$R_2$ is hydrogen; or $C_1$-$C_5$alkyl; especially methyl;
$R_3$ is hydrogen; or $C_1$-$C_5$alkyl;
$R_4$ is hydrogen; or $C_1$-$C_5$alkyl; and
$R_5$ is $C_5$-$C_{20}$alkyl;
and very especially compounds of formula (1) wherein
$R_1$ is hydrogen; $C_1$-$C_5$alkyl, especially isopropyl or methyl; unsubstituted or $C_1$-$C_4$alkyl-substituted phenyl; or pyridino;
$R_2$ is methyl;
$R_3$ and $R_4$ are hydrogen; and
$R_5$ is $C_8$-$C_{18}$alkyl.
Among the last-mentioned compounds very special preference is given to the use of those wherein
$R_5$ is linear $C_8$-$C_{18}$alkyl.
Also preferably used are compounds of formula (1) wherein, in formula (1a),
R"" is hydrogen; or pyridyl-$C_1$-$C_3$alkyl; and
$n_1$ and $n_2$ are each 2.
Preference is also given to the use of compounds of formula (1) wherein
$R_1$ and $R_2$ are each independently of the other hydrogen; $C_1$-$C_5$alkyl; phenyl which is unsubstituted or substituted by halogen, $C_1$-$C_5$alkyl, $C_1$-$C_5$alkoxy or by amino; biphenyl; cyclo-$C_3$-$C_7$alkyl; 3-pyridyl; 4-pyridyl; 2-thiophenyl; 3-thiophenyl; or thiazolyl;
or compounds of formula (1) wherein
$R_3$ is hydrogen; or phenyl;
or compounds of formula (1) wherein
$R_4$ is hydrogen.
Special preference is given to the use of compounds of formula (2)

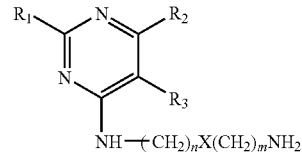

wherein
X is —O—; or

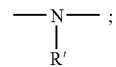

R' is hydrogen; or $C_1$-$C_3$alkyl;
n is 1-3; and
m is 1-3;
and
$R_1$, $R_2$ and $R_3$ are as defined for formula 1.
The Table that follows lists, by way of example, further 4-aminopyrimidines according to the invention:

| Comp. of formula | Structural formula | Purity [%] 254 nm | Purity [%] 280 nm |
|---|---|---|---|
| 3 | | 64 | 72 |
| 4 | | 37 | 96 |
| 5 | | 83 | 97 |
| 6 | | 92 | 97 |
| 7 | | 43 | 48 |

-continued

| Comp. of formula | Structural formula | Purity [%] 254 nm | Purity [%] 280 nm |
|---|---|---|---|
| 8 | | 82 | 93 |
| 9 | | 94 | 98 |
| 10 | | 49 | 59 |
| 11 | | 75 | 89 |
| 12 | | 95 | 97 |
| 13 | | 94 | 99 |

-continued

| Comp. of formula | Structural formula | Purity [%] 254 nm | Purity [%] 280 nm |
|---|---|---|---|
| 14 | | 91 | 97 |
| 15 | | 91 | 98 |
| 16 | | 42 | 44 |
| 17 | | 39 | 43 |
| 18 | | 42 | 51 |

-continued

| Comp. of formula | Structural formula | Purity [%] 254 nm | Purity [%] 280 nm |
|---|---|---|---|
| 19 | | 64 | 70 |
| 20 | | 63 | 77 |
| 21 | | 70 | 82 |
| 22 | | 51 | 65 |

-continued
| Comp. of formula | Structural formula | Purity [%] 254 nm | Purity [%] 280 nm |
|---|---|---|---|
| 23 | 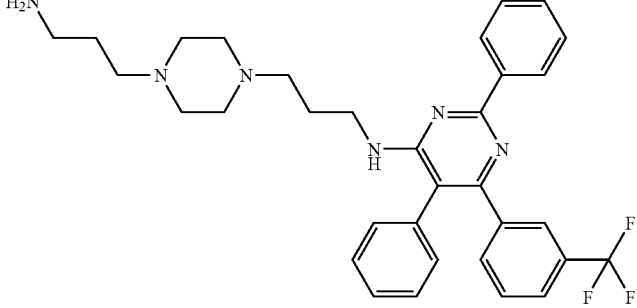 | 67 | 82 |
| 24 | 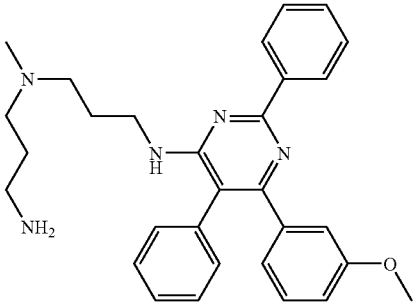 | 95 | 97 |
| 25 | 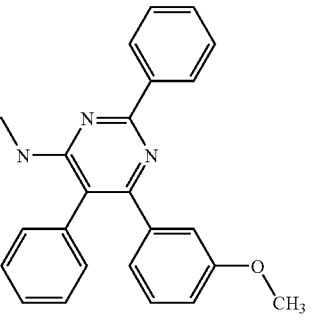 | 88 | 96 |
| 26 | 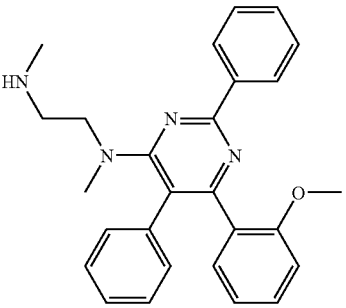 | 81 | 90 |

-continued

| Comp. of formula | Structural formula | Purity [%] 254 nm | Purity [%] 280 nm |
|---|---|---|---|
| 27 | | 88 | 93 |
| 28 | | 86 | 93 |
| 29 | | 61 | 62 |
| 30 | | 85 | 72 |

-continued
| Comp. of formula | Structural formula | Purity [%] 254 nm | Purity [%] 280 nm |
|---|---|---|---|
| 31 | 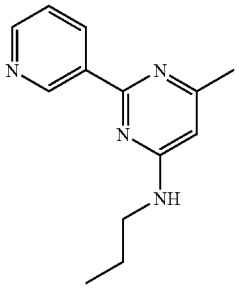 | 45 | 42 |
| 32 | 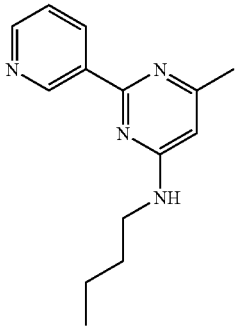 | 69 | 64 |
| 33 | 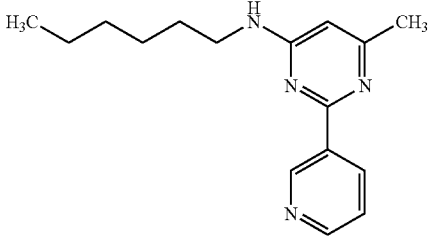 | 94 | 93 |
| 34 | 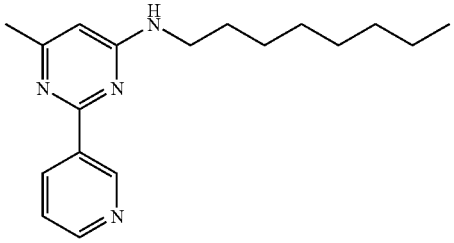 | 89 | 89 |
| 35 | 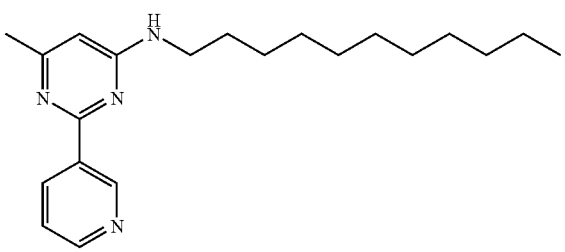 | 92 | 88 |

-continued

| Comp. of formula | Structural formula | Purity [%] 254 nm | Purity [%] 280 nm |
|---|---|---|---|
| 36 | | 82 | 73 |
| 37 | | 82 | 66 |
| 38 | | 56 | 34 |
| 39 | | 67 | 46 |
| 40 | | 43 | 44 |

-continued

| Comp. of formula | Structural formula | Purity [%] 254 nm | Purity [%] 280 nm |
|---|---|---|---|
| 41 | | 81 | 77 |
| 42 | | 91 | 92 |
| 43 | | 72 | 68 |
| 44 | | 88 | 84 |
| 45 | | 82 | 83 |
| 46 | | 88 | 88 |

-continued

| Comp. of formula | Structural formula | Purity [%] 254 nm | Purity [%] 280 nm |
|---|---|---|---|
| 47 | | 72 | 67 |
| 48 | | 81 | 85 |
| 49 | | 92 | 84 |
| 50 | | 84 | 86 |
| 51 | | 77 | 73 |

-continued
| Comp. of formula | Structural formula | Purity [%] 254 nm | Purity [%] 280 nm |
|---|---|---|---|
| 52 | 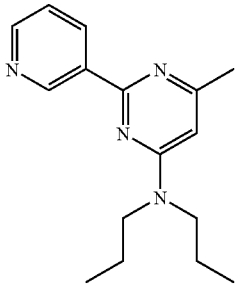 | 88 | 91 |
| 53 | 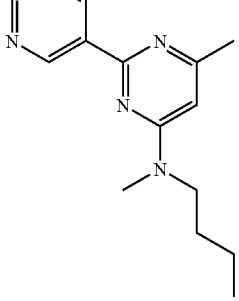 | 87 | 89 |
| 54 | 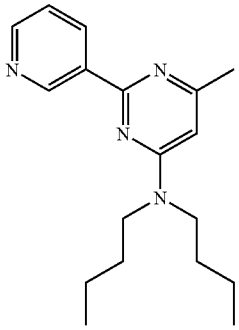 | 90 | 91 |
| 55 | 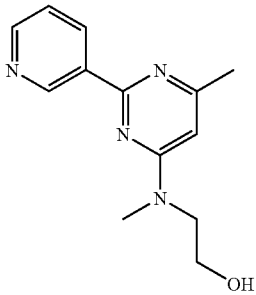 | 85 | 87 |

-continued

| Comp. of formula | Structural formula | Purity [%] 254 nm | Purity [%] 280 nm |
|---|---|---|---|
| 56 | | 87 | 84 |
| 57 | | 99 | 99 |
| 58 | | 58 | 78 |
| 59 | | 34 | 64 |
| 60 | | 46 | 32 |

-continued

| Comp. of formula | Structural formula | Purity [%] 254 nm | Purity [%] 280 nm |
|---|---|---|---|
| 61 | | 90 | 87 |
| 62 | | 66 | 61 |
| 63 | | 99 | 95 |
| 64 | | 80 | 80 |
| 65 | | 96 | 92 |
| 66 | | 90 | 95 |

-continued
| Comp. of formula | Structural formula | Purity [%] 254 nm | Purity [%] 280 nm |
|---|---|---|---|
| 67 | 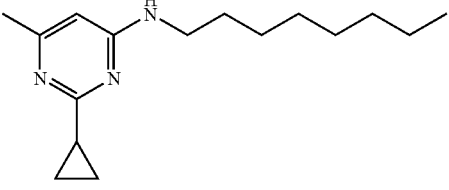 | 48 | 44 |
| 68 | 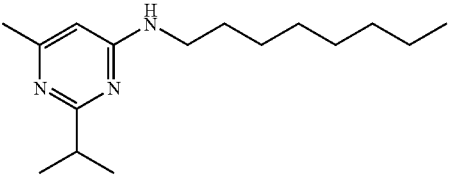 | 37 | 38 |
| 69 | 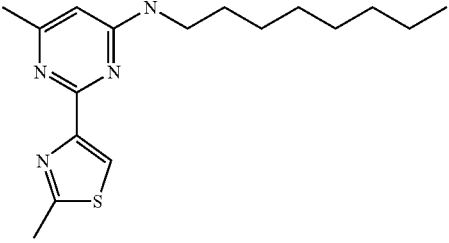 | 64 | 79 |
| 70 | 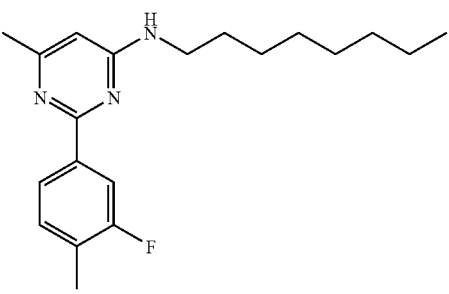 | 71 | 82 |
| 71 | 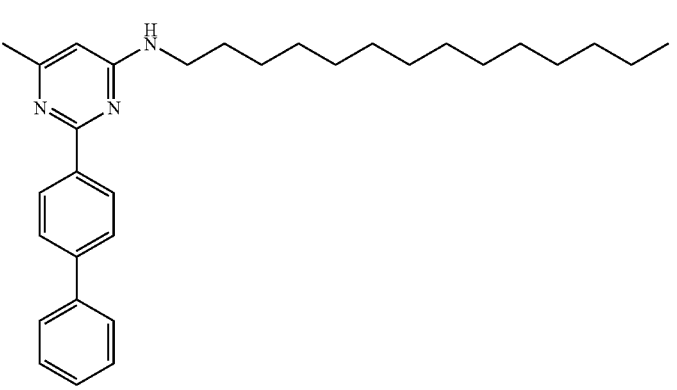 | 88 | 88 |

-continued
| Comp. of formula | Structural formula | Purity [%] 254 nm | Purity [%] 280 nm |
|---|---|---|---|
| 72 | 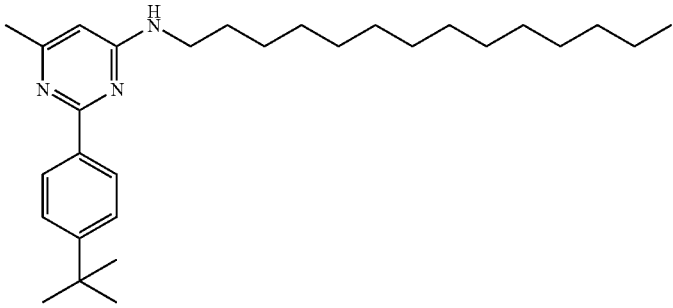 | 79 | 52 |
| 73 | 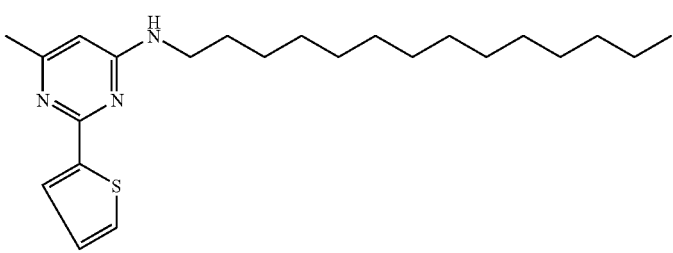 | 90 | 96 |
| 74 | 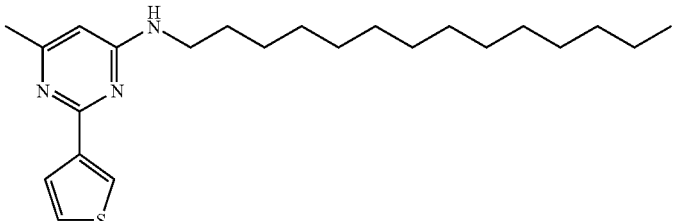 | 79 | 39 |
| 75 | 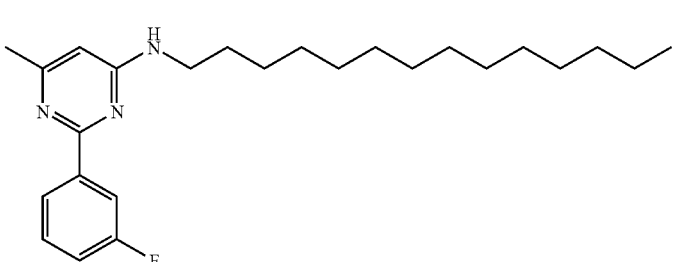 | 92 | 89 |
| 76 | 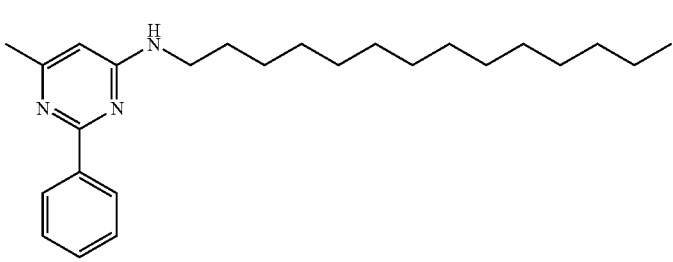 | 97 | 95 |

-continued

| Comp. of formula | Structural formula | Purity [%] 254 nm | Purity [%] 280 nm |
|---|---|---|---|
| 77 | 6-methyl-2-(pyridin-4-yl)-N-tetradecylpyrimidin-4-amine | 86 | 90 |
| 78 | 2,6-dimethyl-N-tetradecylpyrimidin-4-amine | 90 | 94 |
| 79 | 6-methyl-N-tetradecyl-2-(p-tolyl)pyrimidin-4-amine | 92 | 95 |
| 80 | 2-cyclopropyl-6-methyl-N-tetradecylpyrimidin-4-amine | 54 | 50 |
| 81 | 2-isopropyl-6-methyl-N-tetradecylpyrimidin-4-amine | 40 | 42 |
| 82 | 6-methyl-2-(2-methylthiazol-4-yl)-N-tetradecylpyrimidin-4-amine | 67 | 84 |

-continued
| Comp. of formula | Structural formula | Purity [%] 254 nm | Purity [%] 280 nm |
|---|---|---|---|
| 83 | 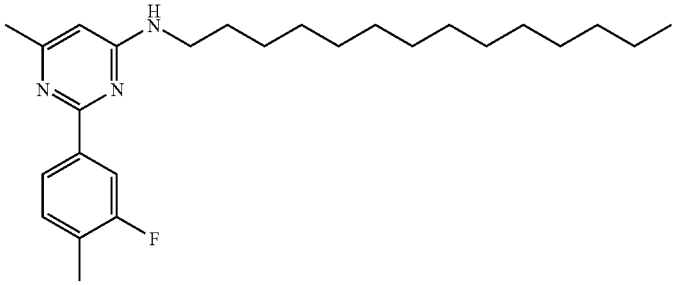 | 77 | 72 |
| 84 | 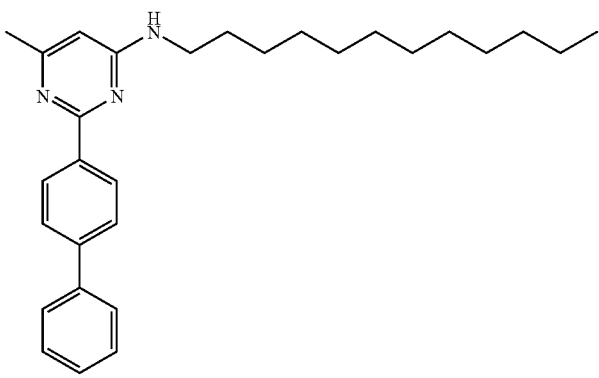 | 93 | 91 |
| 85 | 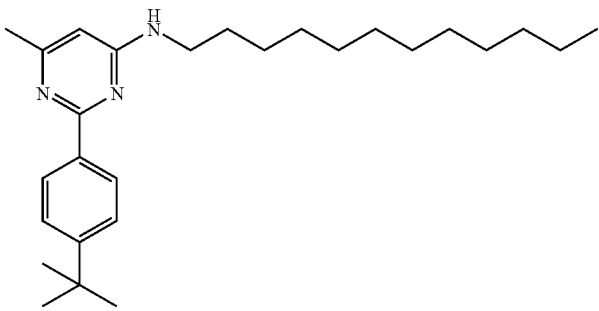 | 83 | 80 |
| 86 | 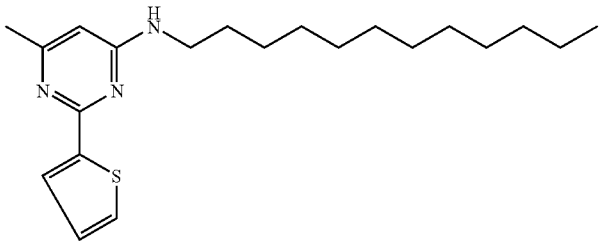 | 92 | 92 |
| 87 | 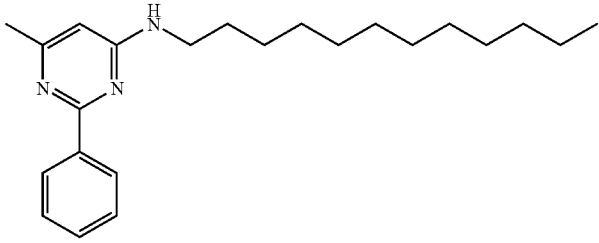 | 95 | 94 |

-continued
| Comp. of formula | Structural formula | Purity [%] 254 nm | Purity [%] 280 nm |
|---|---|---|---|
| 88 |  | 94 | 95 |
| 89 | 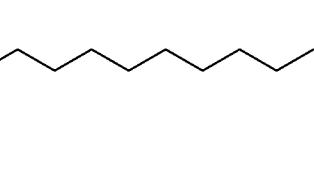 | 92 | 90 |
| 90 | 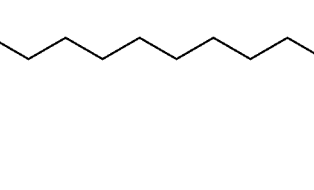 | 54 | 33 |
| 91 | 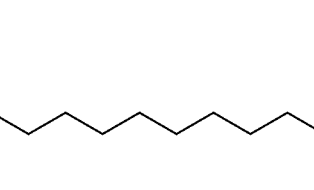 | 89 | 95 |
| 92 |  | 52 | 48 |
| 93 | 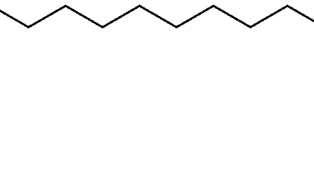 | 40 | 39 |

-continued
| Comp. of formula | Structural formula | Purity [%] 254 nm | Purity [%] 280 nm |
|---|---|---|---|
| 94 | 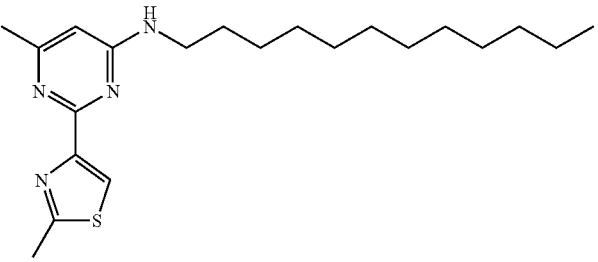 | 65 | 80 |
| 95 | 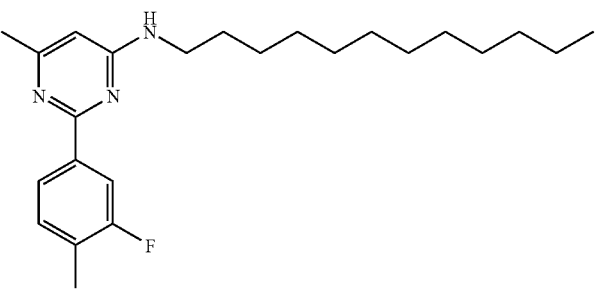 | 82 | 83 |
| 96 | 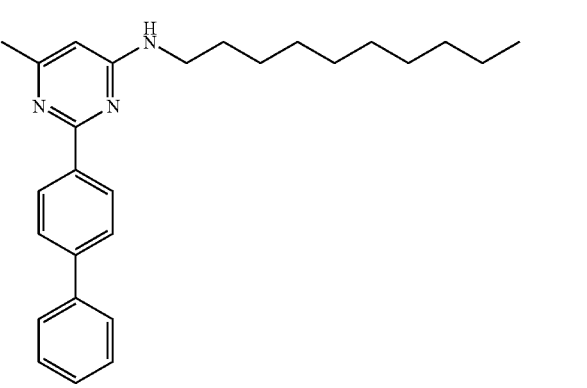 | 78 | 85 |
| 97 | 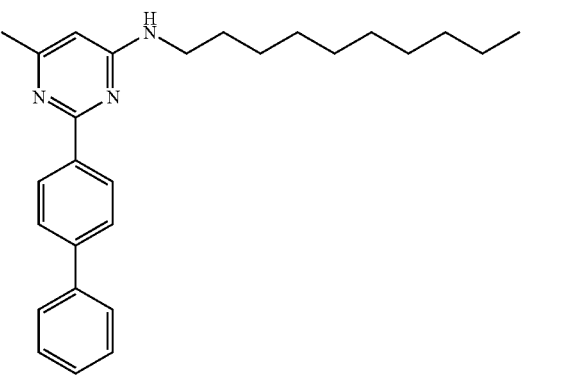 | 31 | 26 |

-continued
| Comp. of formula | Structural formula | Purity [%] 254 nm | Purity [%] 280 nm |
|---|---|---|---|
| 98 | 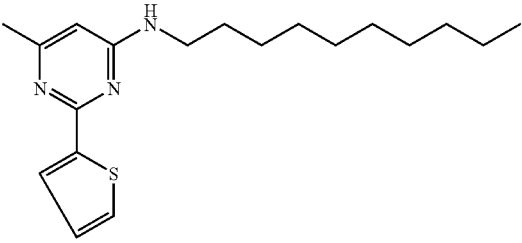 | 79 | 60 |
| 99 | 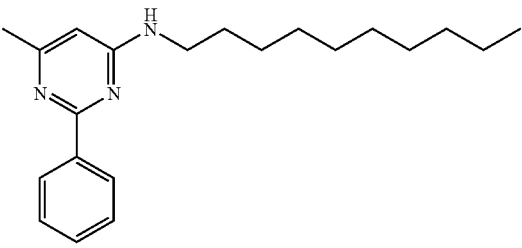 | 93 | 90 |
| 100 | 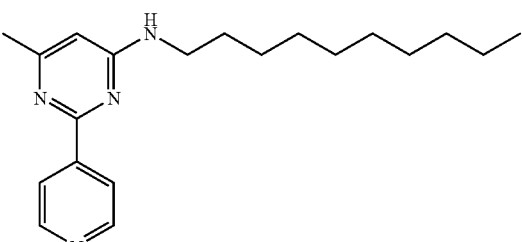 | 71 | 59 |
| 101 | 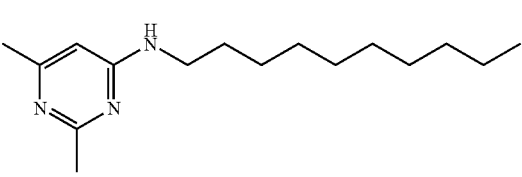 | 87 | 78 |
| 102 | 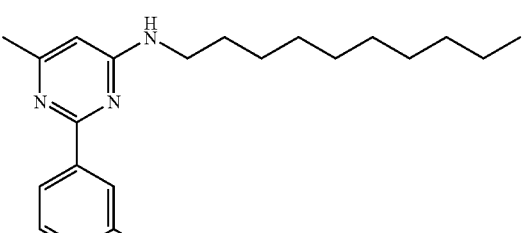 | 49 | 25 |
| 103 | 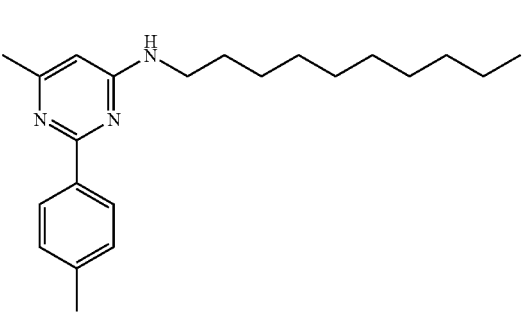 | 89 | 89 |

-continued
| Comp. of formula | Structural formula | Purity [%] 254 nm | Purity [%] 280 nm |
|---|---|---|---|
| 104 | 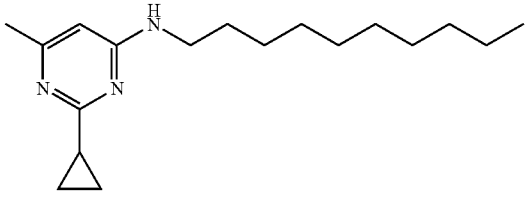 | 54 | 41 |
| 105 | 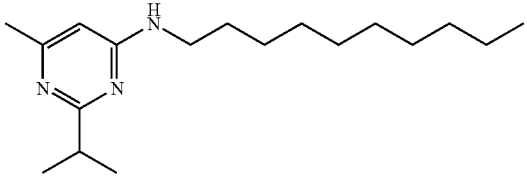 | 33 | 38 |
| 106 | 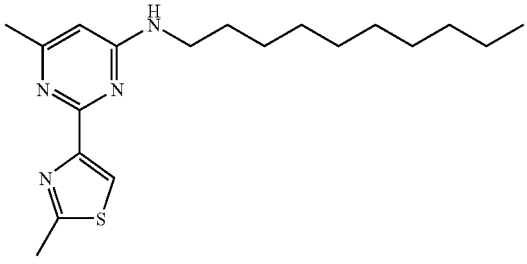 | 65 | 75 |
| 107 | 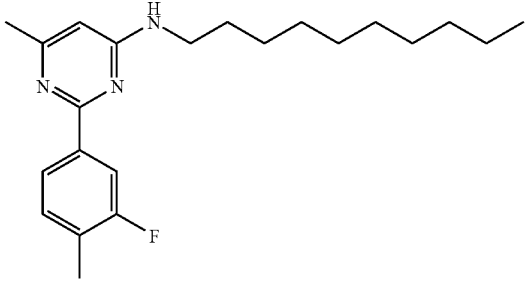 | 80 | 82 |
| 108 | 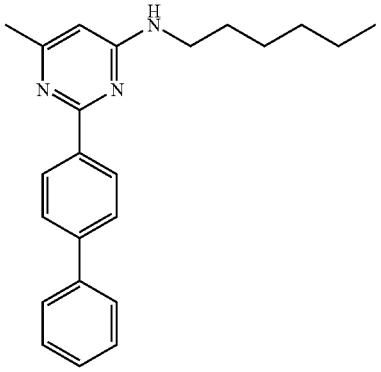 | 87 | 96 |

-continued

| Comp. of formula | Structural formula | Purity [%] 254 nm | Purity [%] 280 nm |
|---|---|---|---|
| 109 | | 87 | 87 |
| 110 | | 90 | 94 |
| 111 | | 94 | 92 |
| 112 | | 87 | 90 |
| 113 | | 92 | 85 |
| 114 | | 41 | 28 |

-continued

| Comp. of formula | Structural formula | Purity [%] 254 nm | Purity [%] 280 nm |
|---|---|---|---|
| 115 | | 93 | 96 |
| 116 | | 58 | 46 |
| 117 | | 39 | 40 |
| 118 | | 54 | 70 |
| 119 | | 82 | 87 |

-continued

| Comp. of formula | Structural formula | Purity [%] 254 nm | Purity [%] 280 nm |
|---|---|---|---|
| 120 | | 42 | 35 |
| 121 | | 87 | 90 |
| 122 | | 78 | 87 |
| 123 | | 68 | 73 |
| 124 | | 93 | 96 |

-continued

| Comp. of formula | Structural formula | Purity [%] 254 nm | Purity [%] 280 nm |
|---|---|---|---|
| 125 | | 93 | 93 |
| 126 | | 87 | 86 |
| 127 | | 65 | 69 |
| 128 | | 46 | 52 |
| 129 | | 58 | 69 |
| 130 | | 82 | 83 |

-continued
| Comp. of formula | Structural formula | Purity [%] 254 nm | Purity [%] 280 nm |
|---|---|---|---|
| 131 | 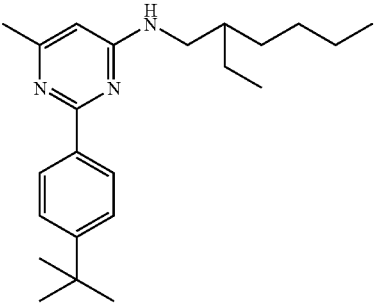 | 73 | 74 |
| 132 | 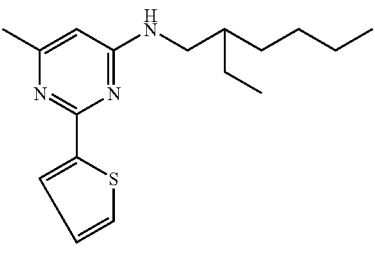 | 88 | 90 |
| 133 | 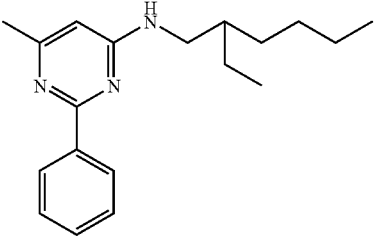 | 94 | 93 |
| 134 | 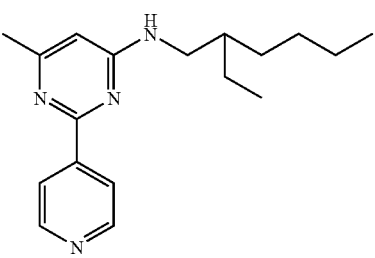 | 100 | 89 |
| 135 | 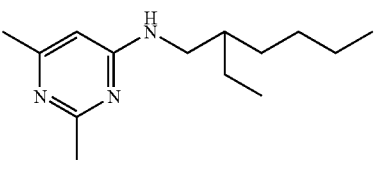 | 92 | 91 |

-continued
| Comp. of formula | Structural formula | Purity [%] 254 nm | Purity [%] 280 nm |
|---|---|---|---|
| 136 | 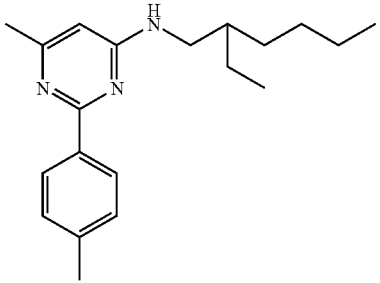 | 92 | 92 |
| 137 | 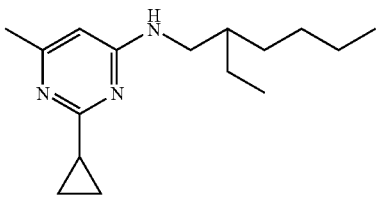 | 49 | 44 |
| 138 | 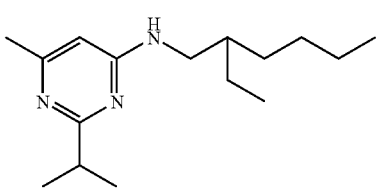 | 41 | 41 |
| 139 | 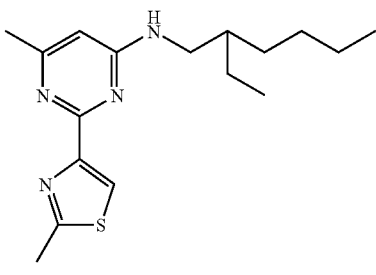 | 50 | 66 |
| 140 | 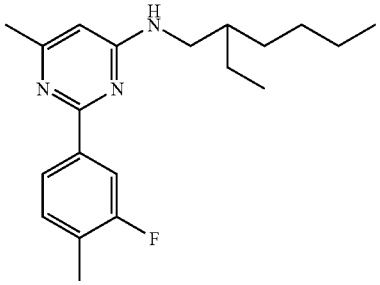 | 100 | 80 |
| 141 | 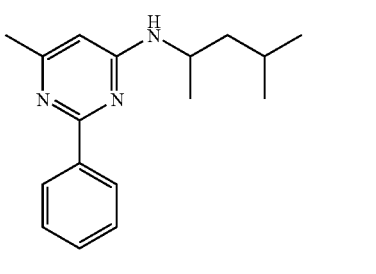 | 74 | 71 |

-continued

| Comp. of formula | Structural formula | Purity [%] 254 nm | Purity [%] 280 nm |
|---|---|---|---|
| 142 | | 100 | 83 |
| 143 | | 84 | 79 |
| 144 | | 62 | 54 |
| 145 | | 43 | 39 |
| 146 | | 34 | 35 |
| 147 | | 61 | 73 |

-continued
| Comp. of formula | Structural formula | Purity [%] 254 nm | Purity [%] 280 nm |
|---|---|---|---|
| 148 | 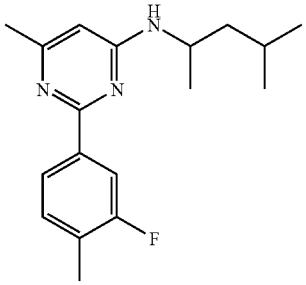 | 72 | 70 |
| 149 | 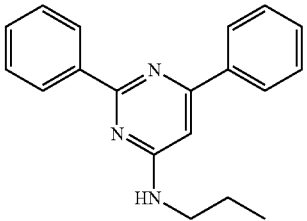 | 91 | 89 |
| 150 | 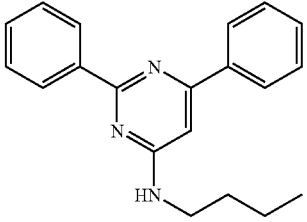 | 87 | 88 |
| 151 | 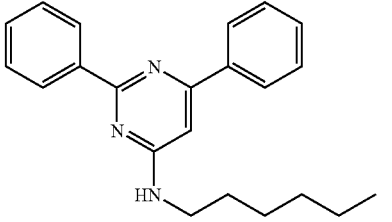 | 88 | 86 |
| 152 | 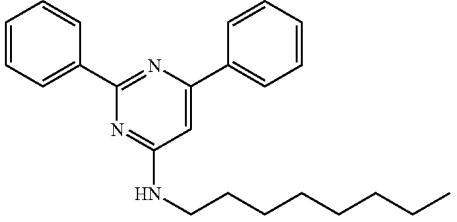 | 91 | 83 |
| 153 | 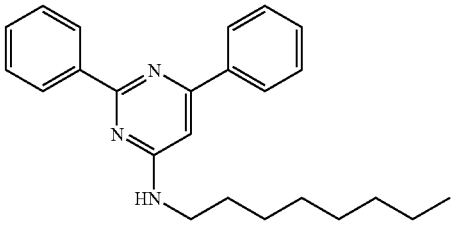 | 89 | 85 |

-continued

| Comp. of formula | Structural formula | Purity [%] 254 nm | Purity [%] 280 nm |
|---|---|---|---|
| 154 | 2,6-diphenyl-N-undecylpyrimidin-4-amine | 94 | 85 |
| 155 | 2,6-diphenyl-N-dodecylpyrimidin-4-amine | 85 | 81 |
| 156 | 2,6-diphenyl-N-tridecylpyrimidin-4-amine | 86 | 82 |
| 157 | 2,6-diphenyl-N-pentadecylpyrimidin-4-amine | 62 | 63 |
| 158 | N-isopropyl-2,6-diphenylpyrimidin-4-amine | 86 | 92 |
| 159 | N-cyclopropyl-2,6-diphenylpyrimidin-4-amine | 89 | 91 |

-continued
| Comp. of formula | Structural formula | Purity [%] 254 nm | Purity [%] 280 nm |
|---|---|---|---|
| 160 | 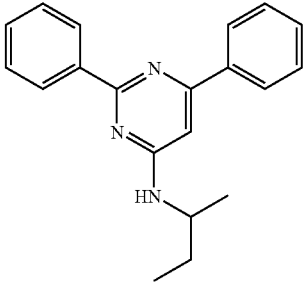 | 88 | 92 |
| 161 | 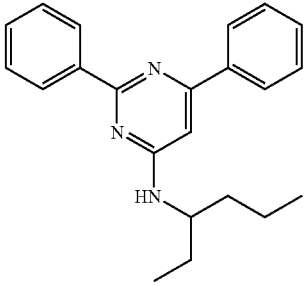 | 87 | 92 |
| 162 | 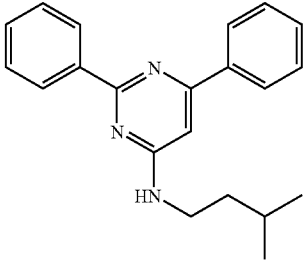 | 67 | 88 |
| 163 | 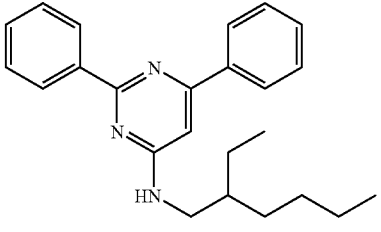 | 67 | 66 |
| 164 | 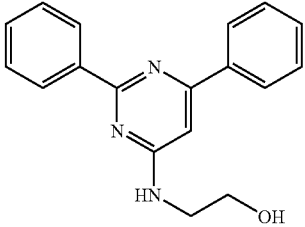 | 85 | 92 |

-continued

| Comp. of formula | Structural formula | Purity [%] 254 nm | Purity [%] 280 nm |
|---|---|---|---|
| 165 | 2,6-diphenyl-pyrimidin-4-yl-NH-(CH2)5-OH | 81 | 92 |
| 166 | 2,6-diphenyl-pyrimidin-4-yl-NH-CH(Et)-CH2-OMe | 68 | 75 |
| 167 | 2,6-diphenyl-pyrimidin-4-yl-NH-(CH2)3-N(Et)2 | 92 | 89 |
| 168 | 2,6-diphenyl-pyrimidin-4-yl-NH-cyclohexyl | 72 | 73 |
| 169 | 2,6-diphenyl-pyrimidin-4-yl-NH-CH2-CH2-phenyl | 87 | 83 |

-continued

| Comp. of formula | Structural formula | Purity [%] 254 nm | Purity [%] 280 nm |
|---|---|---|---|
| 170 | | 77 | 85 |
| 171 | | 86 | 81 |
| 172 | | 87 | 72 |
| 173 | | 69 | 67 |
| 174 | | 66 | 87 |
| 175 | | 69 | 64 |

-continued

| Comp. of formula | Structural formula | Purity [%] 254 nm | Purity [%] 280 nm |
|---|---|---|---|
| 176 | | 82 | 57 |
| 177 | | 87 | 92 |
| 178 | | 77 | 69 |
| 179 | | 77 | 85 |

The 4-aminopyrimidines used in accordance with the invention are prepared by methods known per se (J. Org. Chem.; 1967, 32, 1591). For that purpose, a cyano compound ($R_1$—C≡N) is reacted, in a suitable solvent such as, for example, methanol, ethanol, isopropanol, DMF, tetrahydrofuran etc., with ammonium acetate or ammonium chloride at a temperature of from −10° C. to 100° C. over a period of from 1 hour to 24 hours to form the corresponding amidine compound

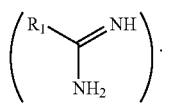

The amidine compound is then condensed with an appropriate β-keto ester

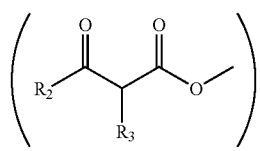

using an auxiliary base such as, for example, sodium carbonate, potassium hydroxide, sodium ethanolate, sodium methanolate, potassium tert-butanolate etc., in a suitable solvent such as, for example, methanol, ethanol, butanol, tert-butanol, THF, DMF, acetonitrile, toluene, xylene etc., over a period of from 1 to 24 hours at a temperature of from 40 to 120° C.

The 4-hydroxy-2-pyrimidine compound

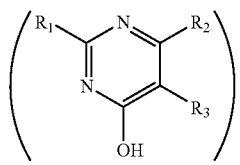

thereby obtained is then converted into the corresponding 4-chloro-2-pyrimidine compound

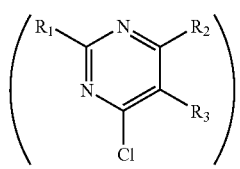

by conventional methods using phosphorus oxychloride.

The substituted 4-aminopyrimidines

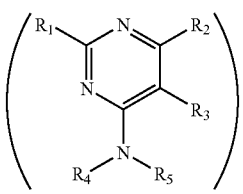

are obtained by reacting the 4-chloro-2-pyrimidine compound with a primary or secondary amine ($R_4R_5NH$) in a suitable solvent such as, for example, DMF, dioxane, toluene, xylene, ethanol, butanol, and an auxiliary base such as, for example, triethylamine, DIEA, sodium carbonate, potassium hydroxide etc., or using an excess of amine at from 40 to 130° C. over a period of from 1 to 24 hours.

The entire reaction proceeds according to the following scheme:

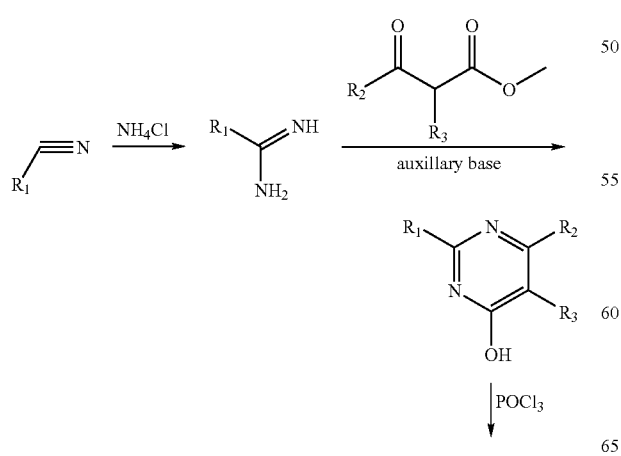

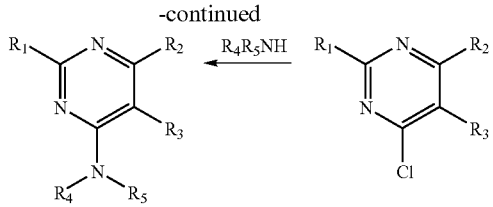

$R_1$, $R_2$, $R_3$, $R_4$ and $R_5$ being as defined for formula (1).

Preparation of the compounds of formula (2) is carried out by reacting an excess of from 2 to 10 equivalents of the diamine compound $H_2N(CH_2)_nX(CH_2)_mNH_2$ in, for example, DMF, dichloromethane, THF or dioxane with trityl chloride polystyrene resin at a temperature of from 10 to 50° C. over a period of from 0.5 to 24 hours. From 2 to 10 equivalents of the appropriately substituted 4,6-dichloropyrimidines

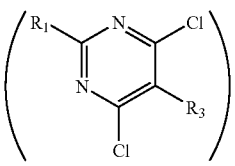

are then reacted, in a suitable solvent such as, for example, dichloromethane, DMF, THF or toluene, with the polymer-bound diamines at from 10 to 120° C. over a period of from 2 to 48 hours. The 4-chloropyrimidines are reacted with from 2 to 10 equivalents of various boronic acids, from 1 to 10% of palladium catalyst and from 2 to 10 equivalents of auxiliary base such as, for example, $CaCO_3$ and $NaCO_3$, in, for example, THF, DMF or dioxane. After washing the resin to remove the excess, the target compounds are split off using from 1 to 30% trifluoroacetic acid (TFA) in dichloromethane (DCM) at 25° C. over a period of from 1 to 5 hours. For the purpose of further purification, the substances are freeze-dried from tBuOH/water 4:1 with from 1 to 10% HOAc and once from tBuOH/water 4:1.

The entire reaction proceeds according to the following scheme:

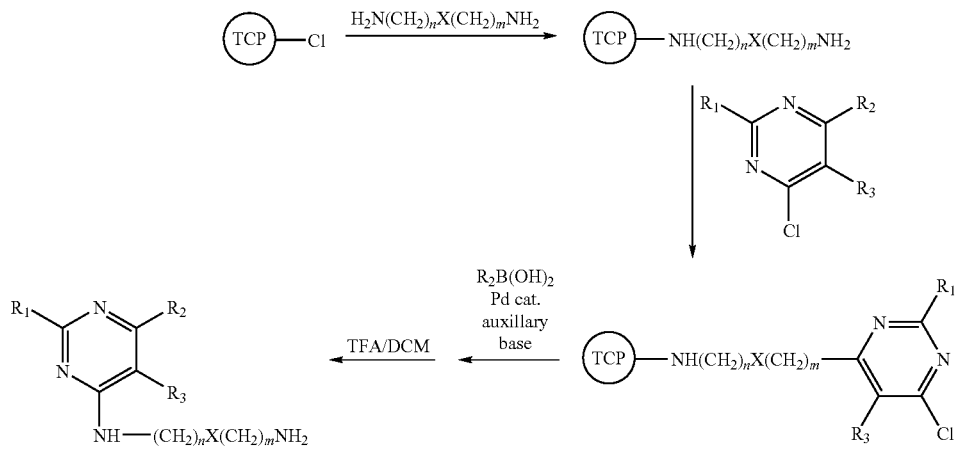

$R_1$, $R_2$, $R_3$, X, m and n being as defined for formula (2).

Some of the 4-aminopyrimidines used in accordance with the invention are known from the literature and some are novel compounds. The invention relates also to those novel compounds.

The novel compounds correspond to formula

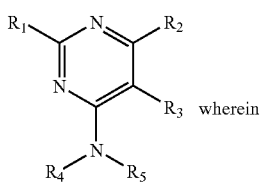

(1') wherein $R_1$ and $R_2$ are each independently of the other hydrogen; $C_1$-$C_5$alkyl which is unsubstituted or substituted by one or more halogen atoms; biphenyl or $C_6$-$C_{10}$aryl which is unsubstituted or substituted by halogen, $C_1$-$C_5$alkyl, $C_1$-$C_5$alkoxy or by amino; a 5- to 7-membered heteroaryl radical; or cyclo-$C_3$-$C_7$alkyl;

$R_3$ is hydrogen; phenyl or $C_1$-$C_5$alkyl which is unsubstituted or substituted by one or more halogen atoms;

$R_4$ is hydrogen; $C_1$-$C_{10}$alkyl; phenyl; or a 5- to 7-membered heteroaryl radical;

$R_5$ is $C_1$-$C_{20}$alkyl which is unsubstituted or substituted by one or more halogen atoms or by a heterocyclic radical or interrupted by one or more —O— or

groups or by a bivalent heterocyclic radical; NR''R'''-$C_1$-$C_{20}$alkyl which is unsubstituted or substituted by a heterocyclic radical or interrupted by one or more —O— or

groups or by a bivalent heterocyclic radical; cyclo-$C_5$-$C_8$alkyl; hydroxy-$C_1$-$C_{20}$alkyl; phenyl-$C_1$-$C_3$alkyl; a heterocyclic radical; or $R_4$ and $R_5$, together with the nitrogen atom linking them, form a radical of formula (1a)

R' is hydrogen; or $C_1$-$C_3$alkyl;
R'' and R''' are each independently of the other hydrogen; $C_1$-$C_5$alkyl; or hydroxy-$C_1$-$C_5$alkyl;
X is

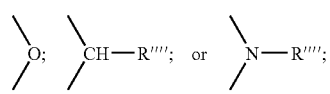

R'''' is hydrogen; $C_1$-$C_4$alkyl; or heteroaryl-$C_1$-$C_4$alkyl; and
$n_1$ and $n_2$ are each independently of the other from 1 to 8;
not including compounds of formula (1') wherein simultaneously
$R_1$ is $C_6$-$C_{10}$aryl; or $C_1$-$C_4$alkyl; and
$R_5$ is $C_1$-$C_7$alkyl.

The 4-aminopyrimidines used in accordance with the invention exhibit pronounced antimicrobial action, especially against pathogenic gram-positive and gram-negative bacteria and against bacteria of the skin flora, and also against yeasts and moulds. They are accordingly suitable especially for disinfection, deodorisation, and for general and antimicrobial treatment of the skin and mucosa and of integumentary appendages (hair), more especially for the disinfection of hands and wounds.

They are accordingly suitable as antimicrobial active substances and preservatives in personal care preparations such as, for example, shampoos, bath additives, haircare preparations, liquid and solid soaps (based on synthetic surfactants and salts of saturated and/or unsaturated fatty acids), lotions and creams, deodorants, other aqueous or alcoholic solutions, e.g. cleansing solutions for the skin, moist cleaning cloths, oils or powders.

The invention accordingly relates also to a personal care preparation comprising at least one compound of formula (1) and cosmetically tolerable carriers or adjuvants.

The personal care preparation according to the invention contains from 0.01 to 15% by weight, preferably from 0.1 to 10% by weight, based on the total weight of the composition, of a compound of formula (1), and cosmetically tolerable adjuvants.

Depending upon the form of the personal care preparation, it comprises, in addition to the 4-aminopyrimidine of formula (1), further constituents such as, for example, sequestering agents, colorants, perfume oils, thickeners or solidifiers (consistency regulators), emollients, UV-absorbers, skin protective agents, antioxidants, additives that improve the mechanical properties, such as dicarboxylic acids and/or aluminium, zinc, calcium or magnesium salts of $C_{14}$-$C_{22}$ fatty acids, and, optionally, preservatives.

The personal care preparation according to the invention may be in the form of a water-in-oil or oil-in-water emulsion, an alcoholic or alcohol-containing formulation, a vesicular dispersion of an ionic or non-ionic amphiphilic lipid, a gel, a solid stick or an aerosol formulation.

As a water-in-oil or oil-in-water emulsion, the cosmetically tolerable adjuvant contains preferably from 5 to 50% of an oil phase, from 5 to 20% of an emulsifier and from 30 to 90% water. The oil phase may comprise any oil suitable for cosmetic formulations such as, for example, one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Cosmetic formulations according to the invention are used in various fields. There come into consideration, for example, especially the following preparations:

skin-care preparations, e.g. skin-washing and cleansing preparations in the form of tablet-form or liquid soaps, synthetic detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascaras, eyeliners, eye creams or eye-fix creams; lip-care preparations, e.g. lipsticks, lip gloss, lip contour pencils, nail-care preparations, such as nail varnish, nail varnish removers, nail hardeners or cuticle removers;

intimate hygiene preparations, e.g. intimate washing lotions or intimate sprays;

foot-care preparations, e.g. foot baths, foot powders, foot creams or foot balsams, special deodorants and antiperspirants or callus-removing preparations;

light-protective preparations, such as sun milks, lotions, creams or oils, sun-blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks; deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

dental care, denture-care and mouth-care preparations, e.g. toothpastes, gel toothpastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidising dyes, or natural hair colorants, such as henna or camomile.

An antimicrobial soap has, for example, the following composition:

0.01 to 5% by weight of a compound of formula (1)
0.3 to 1% by weight titanium dioxide,
1 to 10% by weight stearic acid,
soap base ad 100%, e.g. a sodium salt of tallow fatty acid or coconut fatty acid, or glycerol.

A shampoo has, for example, the following composition:

0.01 to 5% by weight of a compound of formula (1),
12.0% by weight sodium laureth-2-sulfate,
4.0% by weight cocamidopropyl betaine,
3.0% by weight NaCl and
water ad 100%.

A deodorant has, for example, the following composition:

0.01 to 5% by weight of a compound of formula (1),
60% by weight ethanol,
0.3% by weight perfume oil, and
water ad 100%.

The invention relates also to an oral composition containing from 0.01 to 15% by weight, based on the total weight of the composition, of a compound of formula (1), and orally tolerable adjuvants.

Example of an oral composition:

10% by weight sorbitol,
10% by weight glycerol,
15% by weight ethanol,
15% by weight propylene glycol,
0.5% by weight sodium lauryl sulfate,
0.25% by weight sodium methylcocyl taurate,
0.25% by weight polyoxypropylene/polyoxyethylene block copolymer, 0.10% by weight peppermint flavouring,
0.1 to 0.5% by weight of a compound of formula (1), and
48.6% by weight water.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name Olafluor.

The 4-aminopyrimidines of formula (1) used in accordance with the invention are also suitable for treating, especially preserving, textile fibre materials. Such materials are undyed and dyed or printed fibre materials, for example of silk, wool, polyamide or polyurethanes, and especially cellulosic fibre materials of all kinds. Such fibre materials are, for example, natural cellulose fibres, such as cotton, linen, jute and hemp, as well as cellulose and regenerated cellulose. Preferred suitable textile fibre materials are made of cotton.

The 4-aminopyrimidines according to the invention are suitable also for treating, especially imparting antimicrobial properties to or preserving, plastics such as, for example, polyethylene, polypropylene, polyurethane, polyester, polyamide, polycarbonate, latex etc. Fields of use therefor are, for example, floor coverings, plastics coatings, plastics containers and packaging materials; kitchen and bathroom utensils (e.g. brushes, shower curtains, sponges, bathmats), latex, filter materials (air and water filters), plastics articles used in the field of medicine such as, for example, dressing materials, syringes, catheters etc., so-called "medical devices", gloves and mattresses.

Paper, for example papers used for hygiene purposes, may also be provided with antimicrobial properties using the 4-aminopyrimidines according to the invention.

It is also possible for nonwovens such as, for example, nappies/diapers, sanitary towels, panty liners, and cloths for hygiene and household uses, to be provided with antimicrobial properties in accordance with the invention.

The 4-aminopyrimidines of formula (1) are also used in washing and cleaning formulations such as, for example, liquid or powder washing agents or softeners.

The 4-aminopyrimidines of formula (1) can also be used especially in household and general-purpose cleaners for cleaning and disinfecting hard surfaces.

A cleaning preparation has, for example, the following composition:
0.01 to 5% of a compound of formula (1)
3.0% octyl alcohol 4EO
1.3% fatty alcohol $C_8$-$C_{10}$polyglucoside
3.0% isopropanol
water ad 100%.

In addition to preserving cosmetic and household products, the preservation of technical products, the provision of technical products with antimicrobial properties and use as a biocide in technical processes are also possible, for example in paper treatment, especially in paper treatment liquors, printing thickeners of starch or cellulose derivatives, surface-coatings and paints.

The 4-aminopyrimidines of formula (1) are also suitable for the antimicrobial treatment of wood and for the antimicrobial treatment of leather, the preserving of leather and the provision of leather with antimicrobial properties.

The compounds according to the invention are also suitable for the protection of cosmetic products and household products from microbial damage.

The following Examples illustrate, but do not limit, the present invention.

IMPLEMENTATION EXAMPLES

General Work Procedure for Parallel Synthesis of 4-Aminopyrimidines

Example 1

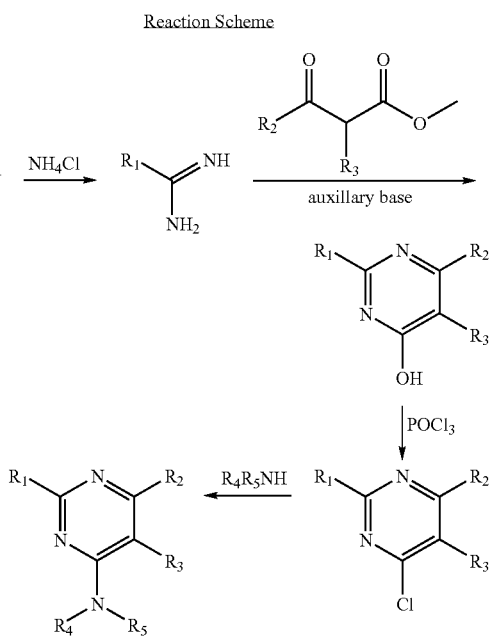

Reaction Scheme

Preparation of 4-chloro-6-methyl-2-phenylpyrimidine 2.2 g of benzamidine hydrochloride (14.05 mmol) are reacted, in 10 ml of absolute EtOH, with 5.43 ml (14.05 mmol) of 20% sodium ethanolate solution and then condensed with 1.66 g of methyl acetoacetate (14.29 mmol) for 4 hours at 90° C.

The crude product is concentrated by evaporation and taken up in 30 ml of toluene.

4.31 g of phosphorus oxychloride (28.1 mmol) are added and the reaction mixture is heated at 120° C. for 3 hours. After cooling to 20° C., the excess is neutralised with sodium hydroxide solution, and the mixture is diluted with ethyl acetate and then washed with water and saturated sodium chloride solution.

The product solution is dried over sodium sulfate and concentrated by evaporation.

2.2 g of 4-chloro-6-methyl-2-phenylpyrimidine (77.7% of theory) are obtained.

Example 2

Reaction of 4-chloro-6-methyl-2-phenylpyrimidine with Monoamines 20.5 mg of 4-chloro-6-methyl-2-phenylpyrimidine (0.1 mmol) are heated with 3 equivalents of monoamines (0.3 mmol) in 0.5 ml of absolute dioxane at 100° C. for 20 hours.

After cooling, the products are concentrated in vacuo, taken up in t-BuOH/water 4/1 and freeze-dried. The end products are analysed by LC-MS.

Example 3

Loading of Trityl Chloride Polystyrene Resin with N,N-bis(3-aminopropyl)methylamines and Reaction with 4,6-dichloro-2,5-diphenylpyrimidine In each case, 50 mg of resin (1.29 mmol/g) are shaken in 1 ml of DMF with 94 mg of N,N-bis(3-aminopropyl)methylamine (0.645 mmol) at 25° C. for 3 hours. The resin is filtered off and washed with DCM, MeOH, THF, MeOH and DCM and dried in vacuo.

The resin is shaken in 1 ml of DMF with 0.194 g of 4,6-dichloro-2,5-diphenylpyrimidine (0.645 mmol) and 90 µl of triethylamine (0.645 mmol) at 25° C. for 3 hours.

The resin is filtered off and washed with DCM, MeOH, THF, MeOH, DCM and MeOH and dried in vacuo.

Example 4

Parallel Reaction of 4-amino-6-chloro-1,5-diphenylpyrimidine-TCP Resins with Various Boronic Acids and Splitting Off The resin is heated with 126.1 g of caesium carbonate (6 eq., 0.387 mmol) and 300 µL of a toluene solution of 0.1 eq. of a palladium catalyst (WO 01/16057) at 95° C. for 15 minutes. After adding 3 eq. of a boronic acid, dissolved in 700 µl of toluene solution, the mixture is heated at 90° C. for 1 hour.

After cooling, the resin is filtered off and washed with DMF, MeOH, THF, MeOH and DCM and dried in vacuo.

The products are split off using 1.5 ml of a 5% TFA/DCM solution at room temperature for 3 hours. The resin is then washed with 1 ml of DCM and 1 ml of MeOH, and the combined solutions are concentrated to dryness by evaporation. The end products are analysed by LC-MS.

Example 5

Preparation of 4-chloro-6-methyl-2-tolylpyrimidine 2.5 g of 4-methyl-benzamidine hydrochloride (14.65 mmol) are reacted in 10 ml of absolute EtOH with 5.66 ml of a 20% solution of sodium ethanolate (14.65 mmol) and then condensed with 1.73 g of methyl acetoacetate (14.88 mmol) at 90° C. for 4 hours. The crude product is concentrated by evaporation and taken up in 30 ml of toluene. 6.74 g of phosphorus oxychloride (44.0 mmol) are added and the reaction mixture is heated at 120° C. for 3 hours. After cooling to 20° C., the excess is neutralised with sodium hydroxide solution, and the mixture is diluted with ethyl acetate, washed with saturated sodium hydrogen carbonate solution and then with water. The product solution is concentrated by evaporation and separated by column chromatography (hexane/EE: 5/1). 2.1 g of 4-chloro-6-methyl-2-tolylpyrimidine (66.5% of theory) are obtained.

NMR: 1H (ppm in DMSO): 2.4, s, 3H; 2.55, s, 3H; 7.3, d, 2H; 7.5, s, 1H; 8.25, d, 2H

Example 6

Reaction of 4-chloro-6-methyl-2-(4-methyl)-phenylpyrimidine with Monoamines 21.9 mg of 4-chloro-6-methyl-2-(4-methyl)-phenylpyrimidine (0.1 mmol) are heated with 3 eq. of monoamines (0.3 mmol) in 0.5 ml of absolute dioxane at 100° C. for 20 hours. After cooling, the products are concentrated in vacuo, taken up in t-BuOH/water 4/1 and freeze-dried. The end products are analysed by LC-MS.

Example 7

Reaction of 4-chloro-6-methyl-2-(4-methyl)-phenylpyrimidine with Octylamine 1.36 g of 4-chloro-6-methyl-2-(4-methyl)-phenylpyrimidine (6.23 mmol) are heated with 886 mg of octylamine (6.85 mmol) and 2.58 g of potassium carbonate (18.68 mmol) in 10 g of dioxane at 100° C. for 48 hours. After cooling, the product is taken up in 100 ml of ethyl acetate and washed with sodium hydroxide solution 0.5 mol/l, saturated sodium hydrogen carbonate solution and water. The product is concentrated in vacuo, taken up in t-BuOH/water 4/1 and freeze-dried.

1.92 g of 4-chloro-6-methyl-2-(4-methyl)-phenylpyrimidine (6.15 mmol, 98.7% of theory) are obtained.

The end product is analysed by NMR, GC-MS and GC.

NMR 1H (ppm in DMSO): 0.9, t, 3H; 1.25, m, 12H; 1.55, m, 2H; 2.25, s, 3H; 2.3, s, 3H; 6.4, s, 1H; 7.1, m, 1H; 7.2, d, 2H; 8.2, d, 2H; (m/z=311);

GC: 95% purity

Example 8

Preparation of 4-chloro-2-isopropyl-6-methylpyrimidine 76.1 g of 2-isopropyl-6-methyl-4-pyrimidinol [2814-20-2] (500 mmol) are dissolved in 300 ml of toluene at 90° C. 80.5 g of phosphorus oxychloride (525 mmol) are added dropwise thereto at from 90 to 103° C., and the reaction mixture is heated at 110° C. for 2 hours. After cooling to 20° C., the reaction mixture is adjusted to pH 8 using 4M sodium hydroxide solution, with cooling. The aqueous phase is separated off and extracted with 100 ml of toluene. The combined organic phases are washed three times with 100 ml of water each time and dried at RT under 2 mbar. 89.7 g (105%; contains toluene) are obtained.

Example 9

Preparation of 4-dodecylamino-2-isopropyl-6-methylpyrimidine (Compound of Formula (93))

79.2 g of 4-chloro-2-isopropyl-6-methylpyrimidine (464.1 mmol) are heated in 100 ml of dioxane at 100° C. A heated solution of 189.3 g of dodecylamine (1021 mmol, 2.2 eq) in 30 ml of dioxane is added dropwise thereto over the course of 2 hours, and the reaction mixture is further heated for 2 hours at 100° C. and for 9 hours at 109° C. After cooling, 400 ml of ethyl acetate and 150 ml of 4M sodium hydroxide solution (600 mmol) are added thereto and the mixture is stirred at 50° C. for 10 minutes. The lower, aqueous phase is discarded, the organic phase is washed with 300 ml of water, and 10 ml of saturated NaCl solution are added thereto. The organic phase is separated off and concentrated, and the excess dodecylamine is distilled in vacuo up to a bath temperature of 160° C. 136.1 g (91.8%); GC purity: 98%

NMR 1H (ppm in CDCl$_3$): 0.7, t, 3H; 1.1, m, 24H; 1.4, m, 2H; 2.15, s, 3H; 2.75, Q, 1H; 3.05, m, 2H; 4.9, s, 1H; 5.8, s, 1H Example 10

Determination of the Minimum Inhibitory Concentration (MIC Value) in Microtitre Plates Nutrient Medium:
Casein/soymeal peptone broth for preparation of pre-cultures of test bacteria and yeast
Examples of Test Organisms:
Bacteria:
*Pseudomonas aeruginosa* CIP A-22 (=PA)
*Escherichia coli* NCTC 8196 (=EC)
*Staphylococcus aureus* ATCC 9144 (=SA)
*Candida albicans* ATCC 10231 (=CA)
Procedure:
The test substances are pre-dissolved in dimethyl sulfoxide (DMSO) and tested in a dilution series of 1:2.
Bacteria and yeast are cultured overnight in CASO broth.
All the test organism suspensions are adjusted to an organism count of 1-5×10$^6$ CFU/ml using 85% sodium chloride solution.
The test substances are pre-pipetted into microtitre plates in amounts of 8 µl per well.
The pre-adjusted organism suspensions are diluted 1:100 in CASO broth and are added in amounts of 192 µl per well to the test substances.
The test batches are incubated for 48 hours at 37° C.
The incubation, the growth is determined on the basis of the turbidity of the test batches (optical density) at 620 nm in a microplate reader.
The minimum inhibitory concentration (MIC value) is the concentration of substance at which (compared to the growth of the control) an appreciable inhibition of growth (≦20% growth) of the test organisms is observed.
Three microtitre plates are used for each test organism and substance concentration. All the substances are tested in duplicate.
The microbiological test results are compiled in Table 2:

TABLE 2

| Comp. of formula | Purity [%] 254 nm | Purity [%] 280 nm | MIC SA | MIC EC | MIC PA | MIC CA |
|---|---|---|---|---|---|---|
| 3 | 64 | 72 | 7.5 | 15 | >120 | 7.5 |
| 4 | 37 | 96 | 7.5 | 30 | >120 | 15 |
| 5 | 83 | 97 | 7.5 | >120 | >120 | >120 |
| 6 | 92 | 97 | 7.5 | 60 | >120 | >120 |
| 7 | 43 | 48 | 15 | 15 | >120 | 30 |
| 8 | 82 | 93 | 30 | 30 | >120 | 120 |
| 9 | 94 | 98 | 15 | 15 | >120 | 30 |
| 10 | 49 | 59 | 15 | 30 | >120 | 30 |
| 11 | 75 | 89 | 7.5 | 15 | >120 | 7.5 |
| 12 | 95 | 97 | 7.5 | 3.75 | 7.5 | 7.5 |
| 13 | 94 | 99 | 15 | 15 | >120 | 30 |
| 14 | 91 | 97 | 15 | 3.75 | 30 | 15 |
| 15 | 91 | 98 | 15 | >120 | >120 | >120 |

TABLE 2-continued

| Comp. of formula | Purity [%] 254 nm | Purity [%] 280 nm | MIC SA | MIC EC | MIC PA | MIC CA |
|---|---|---|---|---|---|---|
| 16 | 42 | 44 | 7.5 | 15 | >120 | 15 |
| 17 | 39 | 43 | 15 | 30 | >120 | 15 |
| 18 | 42 | 51 | 30 | 30 | 120 | 60 |
| 19 | 64 | 70 | 7.5 | 15 | >120 | 8 |
| 20 | 63 | 77 | 15 | 30 | >120 | 15 |
| 21 | 70 | 82 | 7.5 | <3.75 | 7.5 | <3.75 |
| 22 | 51 | 65 | 15 | 15 | >120 | 7.5 |
| 23 | 67 | 82 | 15 | 7.5 | 30 | 7.5 |
| 24 | 95 | 97 | 30 | 15 | 30 | 30 |
| 25 | 88 | 96 | >120 | 60 | >120 | 120 |
| 26 | 81 | 90 | 60 | 60 | >120 | >120 |
| 27 | 88 | 93 | 30 | 30 | >120 | 60 |
| 28 | 86 | 93 | <3.75 | >120 | >120 | >120 |
| 29 | 61 | 62 | 15 | 30 | >120 | 30 |
| 30 | 85 | 72 | 60 | 30 | >120 | 15 |
| 31 | 45 | 42 | 60 | >120 | >120 | 120 |
| 32 | 69 | 64 | 60 | 120 | >120 | 60 |
| 33 | 94 | 93 | 30 | >120 | >120 | 60 |
| 34 | 89 | 89 | 7.5 | 120 | >120 | 30 |
| 35 | 92 | 88 | 15 | 30 | 120 | 30 |
| 36 | 82 | 73 | 7.5 | 15 | 60 | 7.5 |
| 37 | 82 | 66 | 7.5 | 15 | >120 | 7.5 |
| 38 | 56 | 34 | <3.75 | 7.5 | >120 | <3.75 |
| 39 | 67 | 46 | <3.75 | 30 | >120 | 15 |
| 40 | 43 | 44 | 60 | >120 | >120 | 120 |
| 41 | 81 | 77 | 30 | >120 | >120 | 60 |
| 42 | 91 | 92 | <3.75 | 120 | >120 | 30 |
| 43 | 72 | 68 | 60 | >120 | >120 | 120 |
| 44 | 88 | 84 | 120 | >120 | >120 | 120 |
| 45 | 82 | 83 | 60 | >120 | >120 | 120 |
| 46 | 88 | 88 | 120 | >120 | >120 | 120 |
| 47 | 72 | 67 | 120 | >120 | >120 | >120 |
| 48 | 81 | 85 | 30 | >120 | >120 | 60 |
| 49 | 92 | 84 | 120 | >120 | >120 | >120 |
| 50 | 84 | 86 | 120 | >120 | >120 | >120 |
| 51 | 77 | 73 | 30 | >120 | >120 | >120 |
| 52 | 88 | 91 | 30 | >120 | >120 | 120 |
| 53 | 87 | 89 | 60 | >120 | >120 | 120 |
| 54 | 90 | 91 | 15 | >120 | >120 | 120 |
| 55 | 85 | 87 | 120 | >120 | >120 | >120 |
| 56 | 87 | 84 | 60 | >120 | >120 | 120 |
| 57 | 99 | 99 | 60 | >120 | >120 | 120 |
| 58 | 58 | 78 | 15 | 120 | >120 | 60 |
| 59 | 34 | 64 | 15 | 60 | >120 | 60 |
| 60 | 46 | 32 | 120 | >120 | >120 | 120 |
| 61 | 90 | 87 | 30 | 120 | >120 | 120 |
| 62 | 66 | 61 | 60 | 120 | >120 | 120 |
| 63 | 99 | 95 | 15 | 30 | >120 | 60 |
| 64 | 80 | 80 | 7.5 | 30 | >120 | 15 |
| 65 | 96 | 92 | 30 | 60 | >120 | 15 |
| 66 | 90 | 95 | <3.75 | 30 | >120 | 30 |
| 67 | 48 | 44 | 7.5 | 30 | >120 | 7.5 |
| 68 | 37 | 38 | 15 | 30 | >120 | 15 |
| 69 | 64 | 79 | <3.75 | 30 | >120 | 7.5 |
| 70 | 71 | 82 | <3.75 | 15 | >120 | 7.5 |
| 71 | 88 | 88 | 7.5 | 15 | >120 | 7.5 |
| 72 | 79 | 52 | 7.5 | 15 | >120 | 7.5 |
| 73 | 90 | 96 | <3.75 | 7.5 | >120 | <3.75 |
| 74 | 79 | 39 | <3.75 | 7.5 | >120 | <3.75 |
| 75 | 92 | 89 | 7.5 | 15 | >120 | 7.5 |
| 76 | 97 | 95 | 15 | 60 | >120 | 30 |
| 77 | 86 | 90 | 7.5 | 60 | >120 | 15 |
| 78 | 90 | 94 | <3.75 | 7.5 | >120 | <3.75 |
| 79 | 92 | 95 | <3.75 | <3.75 | >120 | <3.75 |
| 80 | 54 | 50 | <3.75 | 7.5 | >120 | 7.5 |
| 81 | 40 | 42 | <3.75 | <3.75 | >120 | <3.75 |
| 82 | 67 | 84 | <3.75 | 15 | >120 | 7.5 |
| 83 | 77 | 72 | <3.75 | 7.5 | >120 | <3.75 |
| 84 | 93 | 91 | 15 | 15 | >120 | 7.5 |
| 85 | 83 | 80 | 15 | 7.5 | <120 | 7.5 |
| 86 | 92 | 92 | 15 | 15 | >120 | 7.5 |
| 87 | 95 | 94 | 15 | 15 | <120 | 7.5 |
| 88 | 95 | 94 | 15 | 15 | <120 | 7.5 |
| 89 | 92 | 90 | <3.75 | <3.75 | >120 | <3.75 |
| 90 | 54 | 33 | 7.5 | 15 | >120 | <3.75 |
| 91 | 89 | 95 | 30 | 30 | >120 | 15 |

TABLE 2-continued

| Comp. of formula | Purity [%] 254 nm | Purity [%] 280 nm | MIC SA | MIC EC | MIC PA | MIC CA |
|---|---|---|---|---|---|---|
| 92 | 52 | 48 | <3.75 | 15 | >120 | 7.5 |
| 93 | 40 | 39 | <3.75 | 15 | >120 | 7.5 |
| 94 | 65 | 80 | <3.75 | 15 | >120 | 7.5 |
| 95 | 82 | 83 | 15 | 30 | >120 | 15 |
| 96 | 78 | 85 | 15 | 30 | >120 | 15 |
| 97 | 31 | 26 | 7.5 | 15 | >120 | 15 |
| 98 | 79 | 60 | 15 | 15 | >120 | 15 |
| 99 | 93 | 90 | 15 | 15 | >120 | 30 |
| 100 | 71 | 59 | 15 | 15 | >120 | 15 |
| 101 | 87 | 78 | 7.5 | 7.5 | >120 | 7.5 |
| 102 | 49 | 25 | 7.5 | 30 | >120 | 15 |
| 103 | 89 | 89 | 15 | 60 | >120 | 30 |
| 104 | 54 | 41 | <3.75 | 7.5 | >120 | 7.5 |
| 105 | 33 | 38 | 7.5 | 15 | >120 | 7.5 |
| 106 | 65 | 75 | <3.75 | 15 | >120 | 15 |
| 107 | 80 | 82 | 7.5 | 15 | >120 | 15 |
| 108 | 87 | 96 | 30 | >120 | >120 | >120 |
| 109 | 87 | 87 | 15 | 60 | >120 | 30 |
| 110 | 90 | 94 | 60 | >120 | >120 | 120 |
| 111 | 94 | 92 | 7.5 | 120 | >120 | 60 |
| 112 | 87 | 90 | 15 | 120 | >120 | 30 |
| 113 | 92 | 85 | 7.5 | 120 | >120 | 30 |
| 114 | 41 | 28 | 15 | >120 | >120 | 30 |
| 115 | 93 | 96 | 7.5 | >120 | >120 | 120 |
| 116 | 58 | 46 | 7.5 | 60 | >120 | 15 |
| 117 | 39 | 40 | 15 | 120 | >120 | 30 |
| 118 | 54 | 70 | 7.5 | 60 | >120 | 15 |
| 119 | 82 | 87 | 7.5 | >120 | >120 | 120 |
| 120 | 42 | 35 | 30 | 120 | >120 | 30 |
| 121 | 87 | 90 | 30 | >120 | >120 | >120 |
| 122 | 78 | 87 | 30 | >120 | >120 | 120 |
| 123 | 68 | 73 | 120 | >120 | >120 | >120 |
| 124 | 93 | 96 | 60 | 120 | >120 | 60 |
| 125 | 93 | 93 | 120 | >120 | >120 | 120 |
| 126 | 87 | 86 | 120 | >120 | >120 | 120 |
| 127 | 65 | 69 | 60 | >120 | >120 | 60 |
| 128 | 46 | 52 | 120 | >120 | >120 | 120 |
| 129 | 58 | 69 | 120 | >120 | >120 | 120 |
| 130 | 82 | 83 | 120 | >120 | >120 | >120 |
| 131 | 73 | 74 | 120 | >120 | >120 | >120 |
| 132 | 88 | 90 | 60 | >120 | >120 | >120 |
| 133 | 94 | 93 | 15 | >120 | >120 | >120 |
| 134 | 100 | 89 | 7.5 | >120 | >120 | 120 |
| 135 | 92 | 91 | 60 | 120 | >120 | 30 |
| 136 | 92 | 92 | 7.5 | >120 | >120 | 60 |
| 137 | 49 | 44 | 15 | 30 | >120 | 15 |
| 138 | 41 | 41 | 30 | 60 | >120 | 30 |
| 139 | 50 | 66 | 7.5 | 60 | >120 | 30 |
| 140 | 100 | 80 | 15 | >120 | >120 | 120 |
| 141 | 74 | 71 | 120 | >120 | >120 | >120 |
| 142 | 100 | 83 | 30 | >120 | >120 | 120 |
| 143 | 84 | 79 | >120 | >120 | >120 | 120 |
| 144 | 62 | 54 | 60 | >120 | >120 | 120 |
| 145 | 43 | 39 | >120 | >120 | >120 | 120 |
| 146 | 34 | 35 | >120 | >120 | >120 | 120 |
| 147 | 61 | 73 | 60 | >120 | >120 | 120 |
| 148 | 72 | 70 | 120 | >120 | >120 | >120 |

| Example 11: Agar incorporation test CG128e | |
|---|---|
| Medium: | Casein/soymeal peptone agar (Merck) |
| | *Sabouraud 4% glucose agar (Merck) |
| Diluent: | Sterile 0.85% NaCl solution |
| Incubation: | 24 hours at 37° C. |
| | *3 days at 28° C. |
| Test solution: | 1% stock solutions of all the test substances are prepared in a suitable solvent and diluted in serial dilutions to end concentrations of from 1000 ppm to 10 ppm. |

Test Principle:

0.3 ml of each dilution step is mixed with 15 ml of nutrient medium while the latter is still liquid. After the nutrient medium has solidified, 10 μl of each of the following organism dilutions of the test strains in 0.85% NaCl solution are spotted onto the agar medium:

Microorganisms Used:

| | |
|---|---|
| Staphylococcus aureus ATCC 6538 | Staphylococcus aureus ATCC 9144 |
| Staphylococcus epidermidis ATCC 12228 | Corynebacterium xerosis* ATCC 373 |
| C. minutissimum ATCC 23348 | Propionibacterium acnes (*) ATCC 6919 |
| Escherichia coli NCTC 8196 | Escherichia coli ATCC 10536 |
| Proteus vulgaris ATCC 6896 | Klebsiella pneumoniae ATCC 4352 |
| Salmonella choleraesuis ATCC 9184 | Pseudomonas aeruginosa ATCC 15442 |
| Candida albicans ATCC 10231 | Aspergillus niger ATCC 6275 |

The plates are incubated at 37° C. for 24 hours (*A. niger* at 28° C. for 3 days) and then the highest dilution (lowest concentration) of the test substance at which growth is just no longer discernible (corresponds to the MIC) is determined. The results are shown in Table 3.

TABLE 3

| | Compound of formula | | |
|---|---|---|---|
| Microorganism | (36) | (89) | (93) |
| Staphylococcus aureus ATCC 6538 | 120 | 7.5 | 3.75 |
| Staphylococcus aureus ATCC 9144 | 120 | 7.5 | 3.75 |
| Staphylococcus epidermidis ATCC 12228 | >120 | 120 | 3.75 |
| Corynebacterium xerosis* ATCC 373 | 60 | 3.75 | 1.88* |
| C. minutissimum ATCC 23348 | 30 | 3.75 | 1.88 |
| Propionibacterium acnes (*) ATCC 6919 | 60 | 3.75 | 3.75 (*) |
| Escherichia coli NCTC 8196 | 120 | 120 | 120 |
| Escherichia coli ATCC 10536 | >120 | >120 | 120 |
| Proteus vulgaris ATCC 6896 | >120 | 60 | >120 |
| Klebsiella pneumoniae ATCC 4352 | 60** | >120 | 60 |
| Salmonella choleraesuis ATCC 9184 | >120 | >120 | 120 |
| Pseudomonas aeruginosa ATCC 15442 | >120 | >120 | >120 |
| Candida albicans ATCC 10231 | >120 | >120 | >120 |
| Aspergillus niger ATCC 6275 | >120 | >120 | >120 |

Example 12

"Microbicidal Activity" Suspension Test CG 161/EN1040

Test Method:

Nutrient Medium:

Casein/soymeal peptone broth for preparation of pre-cultures of test bacteria

Examples of Test Organisms:

*Staphylococcus aureus* ATCC 6538

*Escherichia coli* ATCC 10536

*Actynomyces viscosus* ATCC 43146

Procedure:

The test substances are dissolved in dimethyl sulfoxide (DMSO) and tested in a concentration of 120 μg/ml.

Bacteria are incubated overnight in CASO broth and adjusted to an organism count of $1-5 \times 10^5$ CFU/ml using 0.85% sodium chloride solution.

The test substances are pre-pipetted into microtitre plates in amounts of 8 μl per well.

The adjusted test organism suspensions are added in amounts of 192 μl per well to the test substances and mixed. After defined contact times, the test batches are mixed, an aliquot is withdrawn and diluted in several steps in a dilution series of 1:10 in a suitable inactivation medium.

The test plates are incubated for 24 hours at 37° C. After incubation, the growth is determined on the basis of the turbidity of the test batches (optical density) at 620 nm in a microplate reader.

On the basis of the number of steps in the dilution series that exhibit growth, the reduction in the test organism concentration is determined in powers of ten (log value).

One microtitre plate is used for each test organism.

All the substances are tested in duplicate.

The results (log reduction) are shown in Table 4:

TABLE 4

| | | Compound of formula | | | |
|---|---|---|---|---|---|
| Organism | Contact time | (93) 0.12% | (93) 120 ppm | (89) 0.12% | (89) 120 ppm |
| S. aureus | 5 min | >5 | 1.4 | | <1 |
| S. aureus | 30 min | >5 | 3.8 | | 1.7 |
| E. coli | 5 min | >5 | >5 | | 4.6 |
| E. coli | 30 min | >5 | >5 | | >5 |
| A. viscosus | 5 min | >5 | 2 | 4.9 | 3.9 |
| A. viscosus | 30 min | >5 | 4 | >5 | 4.3 |

Example 13

Determination of the Minimum Inhibitory Concentration (MIC Value) in Microtitre Plates Nutrient medium and test procedure correspond to Example 10.

As test organisms there are used:
*Staphylococcus aureus* ATCC 6538
*Escherichia coli* ATCC 10536
*Actynomyces viscosus* ATCC 43146
Microbiological test results are compiled In Table 5:

TABLE 5

| Comp. of formula | Purity [%] 254 nm | Purity [%] 280 nm | MIC SA | MIC EC | MIC AV |
|---|---|---|---|---|---|
| 149 | 91 | 89 | 120 | >120 | 15 |
| 150 | 87 | 88 | 120 | >120 | 60 |
| 151 | 88 | 86 | 120 | >120 | 15 |
| 152 | 91 | 83 | 30 | >120 | 15 |
| 153 | 89 | 85 | 120 | >120 | 30 |
| 154 | 94 | 85 | 120 | 120 | 30 |
| 155 | 85 | 81 | 30 | 30 | 7.5 |
| 156 | 86 | 82 | 7.5 | 15 | <3.75 |
| 157 | 62 | 63 | 15 | >120 | <3.75 |
| 158 | 86 | 92 | >120 | >120 | 7.5 |
| 159 | 89 | 91 | 120 | >120 | 30 |
| 160 | 88 | 92 | 120 | >120 | 15 |
| 161 | 87 | 92 | 120 | >120 | 30 |
| 162 | 67 | 88 | 120 | >120 | 30 |
| 163 | 67 | 66 | >120 | >120 | 60 |
| 164 | 85 | 92 | 120 | >120 | 30 |
| 165 | 81 | 92 | >120 | >120 | 30 |
| 166 | 68 | 75 | >120 | >120 | 30 |
| 167 | 92 | 89 | 120 | 120 | 15 |
| 168 | 72 | 73 | >120 | >120 | 15 |
| 169 | 87 | 83 | >120 | >120 | 30 |
| 170 | 77 | 85 | >120 | >120 | 15 |
| 171 | 86 | 81 | 120 | >120 | 30 |
| 172 | 87 | 72 | 60 | >120 | 15 |

TABLE 5-continued

| Comp. of formula | Purity [%] 254 nm | Purity [%] 280 nm | MIC SA | MIC EC | MIC AV |
|---|---|---|---|---|---|
| 173 | 69 | 67 | 60 | 60 | 15 |
| 174 | 66 | 87 | 120 | >120 | 60 |
| 175 | 69 | 64 | 120 | 120 | 30 |
| 176 | 82 | 57 | 30 | 30 | 7.5 |
| 177 | 87 | 92 | 120 | >120 | 30 |
| 178 | 77 | 69 | 120 | 120 | 30 |
| 179 | 77 | 85 | 120 | 120 | 30 |

What is claimed is:

1. A method for the antimicrobial treatment of a surface, which comprises contacting said surface with a 4-aminopyrimidine of formula

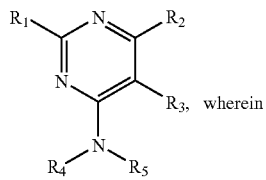

(1)

$R_1$ is biphenyl or $C_6$-$C_{10}$aryl which is unsubstituted or substituted by halogen, $C_1$-$C_5$alkyl, $C_1$-$C_5$alkoxy or by amino;

$R_2$ is biphenyl or $C_6$-$C_{10}$aryl which is unsubstituted or substituted by halogen, $C_1$-$C_5$alkyl, $C_1$-$C_5$alkoxy or by amino;

$R_3$ is phenyl which is unsubstituted or substituted by one or more halogen atoms;

$R_4$ is hydrogen;

$R_5$ is $C_1$-$C_{20}$alkyl substituted by N(R")R''' which alkyl is either further unsubstituted or further substituted by a heterocyclic radical or uninterrupted or interrupted by one or more —O— or

groups or by a bivalent heterocyclic radical; or $R_4$ and $R_5$, together with the nitrogen atom linking them, form a radical of

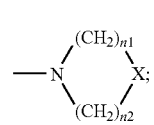

formula (1a)

R' is hydrogen; or $C_1$-$C_3$alkyl;

R" and R''' are each independently of the other hydrogen; $C_1$-$C_5$alkyl; or hydroxy-$C_1$-$C_5$alkyl;

X is

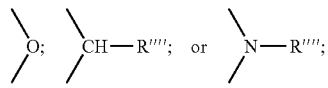

R'''' is hydrogen; $C_1$-$C_4$alkyl; or heteroaryl-$C_1$-$C_4$alkyl; and $n_1$ and $n_2$ are each independently of the other from 1 to 8.

2. A method according to claim 1, wherein $R_5$ is R''R'''N—$C_1$-$C_{20}$alkyl which is uninterrupted or interrupted by one or more —O— or

groups or by a bivalent heterocyclic radical;

R' is hydrogen; or $C_1$-$C_5$alkyl;

R'' and R''' are each independently of the other hydrogen; or methyl.

3. A method according to claim 1, wherein $R_5$ is R''R'''N—$C_1$-$C_{20}$alkyl which is uninterrupted or interrupted by

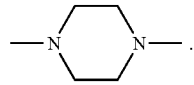

4. A method according to claim 1, wherein $R_5$ is R''R'''N—$C_5$-$C_{20}$alkyl which is uninterrupted or interrupted by one or more —O— or

groups;

R' is hydrogen; or $C_1$-$C_5$alkyl; and

R'' and R''' are each independently of the other hydrogen; or methyl.

5. A method according to claim 4, wherein $R_5$ is R''R'''N—$C_5$-$C_{20}$alkyl; and R'' and R''' are each independently of the other hydrogen; or methyl.

6. A method according to claim 1, wherein $R_4$ is hydrogen.

7. A method according to claim 1, wherein the compound of formula (1) is used in the antimicrobial treatment, deodorisation and disinfection of the skin, mucosa and hair.

8. A method according to claim 1, wherein the compound of formula (1) is used in the treatment of textile fibre materials.

9. A method according to claim 1, wherein the compound of formula (1) is used in preservation.

10. A method according to claim 1, wherein the compound of formula (1) is used in washing and cleaning formulations.

11. A method according to claim 1, wherein the compound of formula (1) is used in imparting antimicrobial properties to, and preserving, plastics, paper, nonwovens, wood or leather.

12. A method for the antimicrobial treatment of a surface according to claim 1, which comprises contacting said surface with a preparation containing 0.01 to 15% by weight of a 4-aminopyrimidine of formula (1).

* * * * *